United States Patent [19]
Krishnan

[11] Patent Number: 5,235,037
[45] Date of Patent: Aug. 10, 1993

[54] VANCOMYCIN PRECIPITATION PROCESS

[75] Inventor: Lalitha Krishnan, Suffern, N.Y.

[73] Assignee: American Cyanamid Company, Stamford, Conn.

[21] Appl. No.: 746,021

[22] Filed: Aug. 15, 1991

[51] Int. Cl.[5] .................... A61K 37/02; C07K 5/12
[52] U.S. Cl. ................................. 530/322; 424/123
[58] Field of Search ..................... 530/322; 424/123

[56] References Cited

U.S. PATENT DOCUMENTS

| | | | |
|---|---|---|---|
| 4,908,351 | 3/1990 | Riva et al. | 435/169 |
| 4,946,941 | 8/1990 | Kondo et al. | 530/317 |
| 5,037,652 | 8/1991 | Catt et al. | 424/123 |

*Primary Examiner*—Howard E. Schain
*Assistant Examiner*—Lynn Touzeau
*Attorney, Agent, or Firm*—H. G. Jackson

[57] ABSTRACT

The invention is an improvement in isolating vancomycin from an aqueous solution of pH 5 to 9 which comprises separating the vancomycin from the solution by adding an alkali or alkaline earth metal inorganic salt to the solution.

18 Claims, No Drawings

VANCOMYCIN PRECIPITATION PROCESS

SUMMARY OF THE INVENTION

The invention is an improvement in the precipitation process for isolating vancomycin from an aqueous solution of pH 5 to 9, the improvement comprising separating the vancomycin from the solution by adding an alkali or alkaline earth metal inorganic salt to the solution.

DESCRIPTION OF THE PRIOR ART

Vancomycin hydrochloride is an amphoteric glycopeptide antibiotic material produced by *Nocardia orientalis* under controlled fermentation conditions. The vancomycins are a closely related group of glycopeptides as described by Barna and Williams Ann. Rev. Microbiol 38, 339(1984). Clinically, vancomycin hydrochloride, has been available commercially since the late 1950's. It is known to bind to mucopeptide precursors terminating in D-Ala-D-Ala and inhibits bacterial cell-wall synthesis residues. In addition, vancomycin also alters cell membrane permeability as well as RNA synthesis.

Vancomycin is used mainly in the treatment of severe infections caused by beta-lactam resistant strains of staphylococci. Vancomycin is the antibiotic of choice in the treatment of susceptible infections of penicillin allergic patients and in the treatment of post-operative diarrhea caused by difficile in the gut.

The commercial preparation of vancomycin is a multistage process which is expensive and also results in loss of product at each stage. Because of the increasing demand for the antibiotic, simpler and more efficient isolation procedures are continually sought.

A method for the preparation of vancomycin by fermentation and its isolation are described in U.S. Pat. No. 3,067,099.

Methods of recovering vancomycin include: precipitation from purified fermentation broths with water miscible non-solvents such as isopropyl alcohol, ethyl alcohol or acetone followed by isolation of the product as shown in U.S. Pat. No. 4,440,753; isolation of the product as a phosphate salt as outlined in EPO 0 145 484; isolation of the product as a copper salt is outlined in U.S. Pat. No. 4,845,194; adjustment of the fermentation broth to pH 7.8 with base and no agitation to precipitate the product as outlined in EPO 0 323 150; as shown in U.S. Pat. No. 4,868,285, by forming an imidazole/vancomycin complex which is harvested by filtration.

The use of cupric salts or imidazole in the isolation process requires the subsequent dissociation of the copper/vancomycin or imidazole/vancomycin complex. This results in a product that is contaminated with copper salts or imidazole. Precipitation of vancomycin by non-solvents like alcohols or acetone results in slurries of vancomycin base that are extremely difficult to filter. An object, when recovering vancomycin from the fermentation broth in which it is produced, is to recover a maximum amount of the antibiotic using a minimum number of steps. Maximum recovery is even more difficult from dilute solutions of the antibiotic. The antibiotic must be isolated from large amounts of a complex aqueous fermentation mixture. The whole fermentation broth in which the antibiotic is produced contains not only the antibiotic, but also insoluble mycelia suspended in a dilute solution of unreacted medium nutrients and miscellaneous metabolic intermediates and products. Isolation of the antibiotic is usually difficult and requires a number of separation, concentration and purification steps.

The present invention provides an improved and convenient method of obtaining vancomycin from dilute aqueous solutions by salting out the product with alkali or alkaline earth metal inorganic salts at pH 5.0 to 9.0.

DETAILED DESCRIPTION

Accordingly, the present invention provides an improved method of isolating vancomycin from fermentation broths. The improved method gives vancomycin directly from fermentation broths with improved filterability and with high recovery in acceptable potency. This is accomplished through the addition of alkali or alkaline earth metal salts such as sodium chloride, lithium chloride, sodium bromide, lithium iodide, potassium iodide, sodium iodide, lithium bromide, sodium solfate, calcium chloride, magnesium chloride, barium chloride and the like to the broth and isolation of the vancomycin free base through filtration.

The process according to the invention may be employed at any stage in the production of the vancomycin. For example, with a whole fermentation broth or a whole broth which has been previously purified by methods such as filtration, extraction, precipitation and/or chromatography. Whole fermentation broth containing the vancomycin used as starting material may be obtained by fermentation of known producing microorganisms under conditions well-known to the art. Thus, for example, vancomycin-containing whole broth may be obtained by fermentation of a producing strain of *Nocardia orientalis* e.g. *Nocardia orientalis* NRRL 2452 using the method described in the U.S. Pat. No. 3,067,099.

Previously, in the commercial preparation of vancomycin, the whole broth is filtered at an alkaline pH of about 8 to 10, the pH of the filtrate is adjusted to about 6 to 7, and the filtrate is then passed across an ion-exchange resin, typically a low cross-linked polystyrene-divinylbenzene cation-exchange resin. Vancomycin is absorbed on the resin. The resin is washed with water and the vancomycin is eluted with an aqueous alkaline solution of pH 9-11. A typical solvent for elution is aqueous sodium hydroxide of pH 10-11. The alkaline eluate containing the vancomycin is neutralized and the activity is further purified by reabsorbing the vancomycin on a non-functional resin, or by isolation as a copper complex.

Thus, in a preferred aspect of the invention we provide a process for separating vancomycin from an aqueous solution thereof in admixture with impurities, which comprises the steps of contacting said aqueous solution with an alkali or alkaline earth metal inorganic salt in a concentration range of 5 to 10% and recovering the vancomycin neutral precipitate thus produced. More preferred is an alkali or alkaline earth metal halide in a concentration of about 10%. Most preferred is sodium chloride.

We have used the method according to the invention to develop a process suitable for the purification of vancomycin present in the fermentation broth obtained from strains of *Nocardia orientalis* producing vancomycin. The new process involves an initial partial purification of the fermented antibiotic by filtration and adsorption chromatography, the purification then being completed by contacting the aqueous solution with an alkali or alkaline earth inorganic salt to precipitate the product which is collected by filtration. The process is simple to operate and provides vancomycin in good yields substantially free of impurities. The improved process of the present invention permits maximum recovery of vancomycin, from dilute aqueous solutions with concentrations as low as 5–6 g/l. At concentrations of 100–150 g/l, the addition of the inorganic salt improves the filterability of the product and permits maximum recovery of the vancomycin neutral.

The process of the present invention affords vancomycin free base that filters with extreme ease and when a partially purified broth is used, the vancomycin obtained is of acceptable purity to be converted into an appropriate acid addition salt for use in formulations for parenteral administration.

The process, according to the invention may be employed at any stage in the production of vancomycin, either with a whole fermentation broth or a whole broth that has been partially purified by filtration and/or chromatography. The purity of the vancomycin free base obtained according to the invention and hence acid addition salt obtained from it will largely depend on the purity of the starting solution utilized.

Thus, in another aspect of the invention we provide a process for the preparation of vancomycin which comprises the steps of (1) filtering a fermentation broth obtained from a strain of *Nocardia orientalis* producing vancomycin and collecting the filtrate, (2) contacting the filtrate with a low crosslinked styrene divinylbenzene cation exchange resin to absorb the vancomycin, (3) eluting the vancomycin from the resin, (4) contacting the vancomycin eluted with a alkali or alkaline earth metal inorganic salt and recovering the precipitated vancomycin thus produced by filtration.

The vancomycin may be removed from the harvested precipitate by redissolving the latter in a suitable solvent such as water containing hydrochloric acid for example at about pH 2. The vancomycin as the hydrochloride may then be precipitated by addition of a suitable non-solvent for vancomycin such as ethanol or isopropanol and harvested by filtration to yield highly pure vancomycin as the hydrochloride salt.

The purity of the vancomycin neutral and the vancomycin hydrochloride is determined by HPLC using a reverse phase column and an ion pair procedure with an acidified acetonitrile-water system.

We have found the process according to the invention to be especially suitable for use with vancomycin.

The invention is further illustrated by the following non-limiting examples.

EXAMPLE 1

Isolation of Vancomycin With Sodium Chloride

To a 100 ml solution of vancomycin neutral[812 ug/mg](94 g/l) is added 10 g of sodium chloride with stirring. The pH is adjusted to 8.0 and stirring is continued for 16 hours. The mixture is filtered and the cake washed with water, dried and assayed. Vancomycin neutral is recovered in 100% yield and has a potency of 926 ug/mg.

EXAMPLE 2

Isolation of Vancomycin with Sodium Chloride

To 100 ml of a solution of vancomycin neutral(100 g/l) is added 10 g of sodium chloride with stirring. The pH is adjusted to 6.0. Stirring is continued for 18 hours and the resulting solid is filtered, dried and assayed. Hplc analysis reveals a potency of 920 ug/mg, and a quantitative recovery of vancomycin.

EXAMPLE 3

Isolation of Vancomycin With Sodium Chloride

Fifty kilograms of moist styrenedivinylbenzene cation exchange resin (2% crosslinking) which is previously loaded with 65 g of vancomycin/kg of wet resin obtained from a standard fermentation run, is suspended in 150 l of deionized water. The slurry is adjusted to pH 7.8 with 50% sodium hydroxide and stirred for 45 minutes. The mix is filtered, and the cake is washed with 50 l of deionized water adjusted to pH 7.8 with 50% sodium hydroxide. The wash is displaced from the cake with air at 40 psig for 15 minutes. The resin filtrate and wash, containing substantial color and little vancomycin is discarded.

The resin is washed once again by repeating the above operations. The twice washed resin is saved for elution of the vancomycin.

A 20 kg portion of the washed resin is eluted with alkali at pH 9–11. The resin eluate is decolorized with carbon.

Solid sodium chloride (14.3 kg) is added to the carbon treated filtrate and wash (120 l, 16.1 g/l vancomycin). The solution is mixed, and the pH is adjusted to 8.0 by the addition of 50% sodium hydroxide. The solution is stirred at 20°–28° C. for 24 hours.

The precipitated vancomycin neutral is filtered and the cake is washed with 20 l of 5% w/v aqueous ammonium chloride solution and 15 l of methanol. The solvent is displaced from the cake by nitrogen at 40 psig for 15 minutes. The cake is dried in vacuo at 40° C. to yield 1806 g of vancomycin neutral assaying 1007 mcg/mg for an overall yield from loaded resin of 69.2%.

EXAMPLE 4

Isolation of Vancomycin with Sodium Chloride

To 500 ml of eluate from a styrenedivinylbenzene cation exchange resin (2% crosslinking) (20.33 g/l) is added 50 g of sodium chloride. The pH is adjusted to 8.0 and stirring is continued for 18 hours. The mixture is filtered and the cake washed with water. Hplc analysis of the solid reveals a potency of 1065 ug/mg.

EXAMPLE 5

Isolation of Vancomycin With Lithium Chloride

To 500 ml of eluate from a styrenedivinylbenzene cation exchange resin (2% cross-linking)(20.33 g/l) is added 50 g of lithium chloride. The pH is adjusted to 8.0 and stirring is continued for 18 hours. The mixture is filtered and the cake washed with water. Hplc analysis of the solid reveals a potency of 980 ug/mg.

EXAMPLE 6

Isolation of Vancomycin With Potassium Chloride

To 500 ml of eluate from a styrenedivinylbenzene cation exchange resin (2% crosslinking)(20.33 g/l) is added 50 g of potassium chloride. The pH is adjusted to 8.0 and stirring is continued for 18 hours. The mixture is filtered and the cake washed with water. Hplc analysis of the solid reveals a potency of 906 ug/mg.

EXAMPLE 7

Isolation of Vancomycin With Barium Chloride

To 500 ml of eluate from a styrenedivinylbenzene cation exchange resin (2% crosslinking)(20.33 g/l) is added 50 g of barium chloride. The pH is adjusted to 8.0 and stirring continued for 18 hours. The mixture is filtered and the cake washed with water. Hplc analysis of the solid reveals a potency of 940 ug/mg.

EXAMPLE 8

Isolation of Vancomycin with Magnesium Chloride

To 500 ml of eluate from a styrenedivinylbenzene cation exchange resin (2% crosslinking)(20.33 g/l) is added 50 g of magnesium chloride. The pH is adjusted to 8.0 and stirring continued for 18 hours. The mixture is filtered and the cake washed with water. Hplc analysis of the solid reveals a potency of 810 ug/mg.

EXAMPLE 9

Isolation of Vancomycin with Calcium Chloride

To 500 ml of eluate from a styrenedivinylbenzene cation exchange resin (2% crosslinking) (20.33 g/l) is added 50 g of calcium chloride. The pH is adjusted to 8.0 and stirring is continued for 18 hours. The mixture is filtered and the cake washed with water. Hplc analysis of the solid reveals a potency of 1065 ug/mg.

EXAMPLE 10

Isolation of Vancomycin with Sodium Bromide

To 500 ml of eluate from a styrenedivinylbenzene cation exchange resin (2% crosslinking) (14.6 g/l) is added 50 g of sodium bromide. The pH is adjusted to 8.0 and stirring is continued for 18 hours. The mixture is filtered and cake washed with water. Hplc analysis of the solid reveals a potency of 1020 ug/mg.

EXAMPLE 11

Isolation of Vancomycin with Potassium Iodide

To 500 ml of eluate from a styrenedivinylbenzene cation exchange resin (2% crosslinking) (14.6 g/l) is added 50 g of potassium iodide. The pH is adjusted to 8.0 and stirring is continued for 18 hours. The mixture is filtered and the cake washed with water. Hplc analysis of the solid reveals a potency of 984 ug/mg.

EXAMPLE 12

Isolation of Vancomycin with Sodium Iodide

To 500 ml of eluate from a styrenedivinylbenzene cation exchange resin (2% crosslinking) (14.6 g/l) is added 50 g of sodium iodide. The pH is adjusted to 8.0 and stirring continued for 18 hours. The mixture is filtered and the cake washed with water. Hplc analysis of the solid reveals a potency of 949 ug/mg.

EXAMPLE 13

Isolation of Vancomycin with Lithium Bromide

To 500 ml of eluate from a styrenedivinylbenzene cation exchange resin (2% crosslinking) 14.6 g/l is added 50 g of lithium bromide. The pH is adjusted to 8.0 and stirring continued for 18 hours. The mixture is filtered and the cake washed with water. Hplc analysis of the solid reveals a potency of 990 ug/mg.

EXAMPLE 14

Isolation of Vancomycin with Potassium Bromide

To 500 of eluate from a styrenedivinylbenzene cation exchange resin (2% crosslinking) (14.6 g/l) is added 50 g of potassium bromide. The pH is adjusted to 8.0 and stirring continued for 18 hours. The mixture is filtered and the cake washed with water. Hplc analysis of the solid reveals a potency of 1011 ug/mg.

EXAMPLE 15

Isolation of Vancomycin with Sodium Sulfate

To 500 ml of eluate from a styrenedivinylbenzene cation exchange resin (2% crosslinking) (14.6 g/l) is added 50 g of sodium sulfate. The pH is adjusted to 8.0 and stirring continued for 18 hours. The mixture is filtered and the cake washed with water. Hplc analysis of the solid reveals a potency of 1012 ug/mg.

We claim:

1. In a process for the isolation of vancomycin from an aqueous solution of pH 5 to 9 the improvement which comprises separating the vancomycin from the solution by adding an alkali or alkaline earth metal inorganic salt to the solution wherein the concentration range of the inorganic salt added is about 5% to about 10%.

2. A process according to claim 1 wherein the pH is between about 7.8 and about 9.0, the temperature is between about 20° C. and about 25° C., the time for precipitation of the Vancomycin to occur is about 16 to about 24 hours and the vancomycin concentration is in the range of 5-200 g/l.

3. The process according to claim 1 wherein the concentration of the alkali or alkaline earth metal inorganic salt is about 10%.

4. The process according to claim 2 wherein the alkali or alkaline earth metal inorganic salt is a alkali or alkaline earth metal inorganic halide.

5. The process according to claim 4 wherein the concentration of the alkali or alkaline earth metal inorganic halide is about 10%.

6. The process according to claim 5 wherein the alkali or alkaline earth metal inorganic halide is sodium chloride.

7. The process according to claim 5 wherein the alkali or alkaline earth metal inorganic halide is potassium chloride.

8. The process according to claim 5 wherein the alkali or alkaline earth metal inorganic halide is lithium chloride.

9. The process according to claim 5 wherein the alkali or alkaline earth metal inorganic halide is barium chloride.

10. The process according to claim 5 wherein the alkali or alkaline earth metal inorganic halide is magnesium chloride.

11. The process according to claim 5 wherein the alkali or alkaline earth metal inorganic halide is calcium chloride.

12. The process according to claim 5 wherein the alkali or alkaline earth metal inorganic halide is sodium bromide.

13. The process according to claim 5 wherein the alkali or alkaline earth metal inorganic halide is potassium iodide.

14. The process according to claim 5 wherein the alkali or alkaline earth metal inorganic halide is sodium iodide.

15. The process according to claim 5 wherein the alkali or alkaline earth metal inorganic halide is lithium bromide.

16. The process according to claim 5 wherein the alkali or alkaline earth metal inorganic halide is potassium bromide.

17. The process according to claim 1 wherein the alkali or alkaline earth metal inorganic salt is sodium sulfate.

18. A process according to claim 1 wherein the concentration of the aqueous solution containing the vancomycin is at least 5 g/l.

* * * * *